United States Patent
Wong et al.

(10) Patent No.: US 9,353,161 B2
(45) Date of Patent: May 31, 2016

(54) STREPTAVIDIN MUTEIN EXHIBITING REVERSIBLE BINDING FOR BIOTIN AND STREPTAVIDIN BINDING PEPTIDE TAGGED PROTEINS

(75) Inventors: Sui-Lam Wong, Calgary (CA); Sau-Ching Wu, Calgary (CA); Isabelle Barrette-Ng, Calgary (CA); Kenneth K-S. Ng, Calgary (CA)

(73) Assignee: UTI LIMITED PARTNERSHIP, Calgary, AB ( * ) Notice: Subject to any disclaimer, the term of this patent is extended or adjusted under 35 U.S.C. 154(b) by 75 days.

(21) Appl. No.: 14/343,883

(22) PCT Filed: Sep. 13, 2012

(86) PCT No.: PCT/IB2012/002212
§ 371 (c)(1),
(2), (4) Date: Jun. 23, 2014

(87) PCT Pub. No.: WO2013/038272
PCT Pub. Date: Mar. 21, 2013

(65) Prior Publication Data
US 2014/0378657 A1    Dec. 25, 2014

Related U.S. Application Data

(60) Provisional application No. 61/534,169, filed on Sep. 13, 2011.

(51) Int. Cl.
| | | |
|---|---|---|
| *C07K 14/315* | (2006.01) | |
| *C07K 17/00* | (2006.01) | |
| *C07K 14/36* | (2006.01) | |
| *C07K 1/22* | (2006.01) | |
| *G01N 33/53* | (2006.01) | |

(52) U.S. Cl.
CPC . *C07K 14/36* (2013.01); *C07K 1/22* (2013.01); *G01N 33/5306* (2013.01); *C07K 2319/20* (2013.01)

(58) Field of Classification Search
CPC .............................. C07K 14/315; C07K 17/00
USPC .......................................................... 530/350
See application file for complete search history.

(56) References Cited

U.S. PATENT DOCUMENTS

| | | |
|---|---|---|
| 6,312,916 B1 | 11/2001 | Kopetzki et al. |
| 6,391,571 B1 | 5/2002 | Kopetzki et al. |
| 6,417,331 B1 | 7/2002 | Kopetzki et al. |

OTHER PUBLICATIONS

Barrette-Ng et al., "The structure of the SBP-Tag-streptavidin complex reveals a novel helical scaffold bridging binding pockets on separate subunits," *Acta Cryst.*, 69:879-887, 2013.
Keefe et al., "One-step purification of recombinant proteins using a nanomolar-affinity streptavidin-binding peptide, the SBP-Tag," *Protein Expression and Purification*, 23:440-446, 2001.
Klumb et al., "Energetic roles of hydrogen bonds at the ureido oxygen binding pocket in the streptavidin-biotin complex," *Biochemistry*, 37(21):7657-7663, 1998.
Lamla and Erdmann, "he Nano-tag, a streptavidin-binding peptide for the purification and detection of recombinant proteins," *Protein Expression and Purification*, 33:39-47 , 2004.
O'Sullivan et al., "Development of a tetrameric streptavidin mutein with reversible biotin binding capability: engineering a mobile loop as an exit door for biotin," *PLoS ONE*, 7(4):e35203, 2012.
PCT International Search Report and Written Opinion issued in International Patent Application No. PCT/IB2012/002212, dated Mar. 19, 2013.
Qureshi et al., "Development and characterization of a series of soluble tetrameric and monomeric streptavidin muteins with differential biotin binding affinities," *The Journal of Biological Chemistry*, 276(49):46422-46428, 2001.
Wu and Wong et al., "Structure-guided design of an engineered streptavidin with reusability to purify streptavidin-binding peptide tagged proteins or biotinylated proteins," *PLoS ONE*, 8(7):e69530, 2013.
Wu and Wong, "Engineering soluble monomeric streptavidin with reversible biotin binding capability," *J. Biol. Chem.*, 280(24): 23225-23231, 2005.

*Primary Examiner* — Maryam Monshipouri
(74) *Attorney, Agent, or Firm* — Parker Highlander PLLC

(57) ABSTRACT

The present invention relates to a new streptavidin muteins. This mutein is binds both streptavidin binding peptide tagged and biotin or biotinylated molecules, and does so in a reversible fashion. As such, it is stable enough to allow reuse, and producible with reasonable production yield via secretion in a soluble functional state without the requirement of refolding via the tedious and expensive denaturation and renaturation processes.

20 Claims, 3 Drawing Sheets

FIGS. 1 A-F

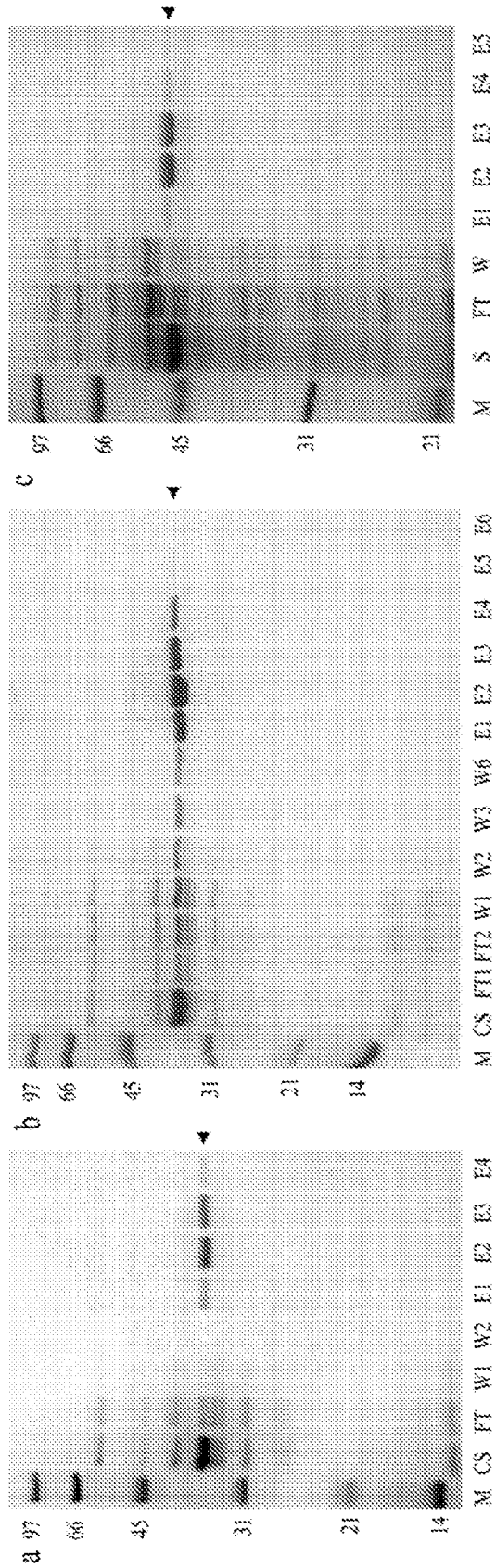
FIGS. 4A-C

STREPTAVIDIN MUTEIN EXHIBITING REVERSIBLE BINDING FOR BIOTIN AND STREPTAVIDIN BINDING PEPTIDE TAGGED PROTEINS

The present application is a national phase application under 35 U.S.C. §371 of International Application No. PCT/IB2012/002212, filed Sep. 13, 2012, which claims benefit of priority to U.S. Provisional Application Ser. No. 61/534,169, filed Sep. 13, 2011. The entire contents of each of the above referenced disclosures are specifically incorporated herein by reference.

The sequence listing that is contained in the file named "UNTIP0124US_ST25.txt", which is 12 KB (as measured in Microsoft Windows®) and was created on Mar. 7, 2014, is filed herewith by electronic submission and is incorporated by reference herein.

BACKGROUND OF THE INVENTION

1. Field of the Invention

The present invention relates to fields of protein biology and diagnostics. More particularly, the present invention relates to improved muteins of streptavidin that specifically yet reversibly bind biotin and strepatavidin binding peptide tagged proteins.

2. Description of Related Art

Wild-type streptavidin is a tetrameric protein with four identical subunits. Two dimers self-associate to form a tetrameric structure. Each subunit can bind one biotin tightly with a dissociation constant ($K_d$) in the range of $10^{-13}$ to $10^{-14}$ M (Wilchek and Bayer, 1990). This binding is considered to be irreversible and streptavidin has been applied to capture and immobilize biotinylated biomolecules. It is widely used in development of many diagnostic kits, biosensor chip, protein and DNA arrays and Western blot studies. However, wild-type streptavidin is not suitable for purification of biotinylated biomolecules. To extend its application, it would be ideal to develop engineered streptavidin muteins with reversible biotin binding ability so that these muteins can be applied to purify biotinylated molecules, to study protein-protein interactions (with one of the interacting proteins to be biotinylated) and to develop reusable biosensor chips and bioreactors. Traditional bioreactors will have enzymes chemically immobilized. After many rounds of usage, bioreactors with the immobilized enzymes will become useless when the immobilized enzymes lose their activities. With an engineered streptavidin that can bind biotin in a reversible manner, one can immobilize these engineered streptavidin proteins to the bioreactor. The enzymes of interest can then be biotinylated and loaded to bioreactors with the immobilized streptavidin muteins to generate functional bioreactors. When the enzymes lose their activity, these inactive enzymes can be eluted off by biotin and the bioreactor can be reloaded with a new batch of biotinylated enzymes.

To develop streptavidin muteins with reversible binding ability, two approaches are common. The first approach is to replace one or more streptavidin amino acid residues that are critical in biotin binding with different residues. These changes can result in lowering the biotin binding affinity in these muteins (Qureshi et al., 2001; U.S. Pat. No. 6,312,916 B1). The second approach is to develop recombinant monomeric streptavidin (Wu and Wong, 2005a). This is based on the fact that a streptavidin subunit does not have a complete biotin binding pocket. A biotin binding pocket in subunit A requires a tryptophan 120 (Trp-120) residue from subunit D. This Trp-120 has been demonstrated to play an important role in biotin binding (Chilkoti et al., 1995).

While purification of biotinylated biomolecules using monomeric avidin offers one of the cleanest approaches, the biotinylation of molecules either chemically or enzymatically requires steps that can be time consuming, labor intensive and costly. To overcome this problem, several streptavidin binding peptide tags have been developed. One of them is the 38-amino-acid streptavidin binding peptide (SBP) tag (Keefe et al., 2001) that can bind streptavidin with high affinity ($K_d$~2.5 nM) without biotinylation. It works well whether the tag is at the N-terminal, internal or C-terminal position of the recombinant protein (Van Leene et al., 2008; Kobayashi et al., 2008). Biotin added to the elution buffer acts as an effective competitor to elute the bound SBP-tagged protein off. However, as streptavidin binds biotin tightly ($K_d$~$10^{-14}$ M) (Green, 1990), the streptavidin matrix essentially can only be used once, and this drawback makes the purification very costly. In order to vitalize this powerful purification technology, it would be ideal to have an engineered streptavidin that not only can bind biotin reversibly, but one that retains a high SBP tag binding strength. The biotin binding strength ($K_d$) of this engineered streptavidin should be ~$10^{-8}$ M. Thus, biotin should be strong enough to displace the SBP tag from streptavidin, but not bind irreversibly to streptavidin. Consequently, the affinity matrix could be regenerated by a simple washing step and can be reused for multiple rounds without using any harsh elution conditions.

SUMMARY OF THE INVENTION

Thus, in accordance with the present invention, there is provided a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine. The mutien may further comprise a serine to alanine substitution at residue 27. The mutein may lack a signal sequence, and may consist of 159 streptavidin residues. The mutein may have the sequence of SEQ ID NO:3. The mutein may comprise a signal sequence, and may consist of 188 streptavidin residues. The mutein may have the sequence of SEQ ID NO:5. The mutein may further comprise a non-streptavidin sequence fused to the mutein, such as a cellulose binding domain, a chitin binding domain, a dextran binding domain, a silica binding peptide, a gold binding peptide or ferritin.

In another embodiment, there is provided a nucleic acid encoding a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine. The nucleic acid may encode a mutein further comprising a serine to alanine substitution at residue 27. The nucleic acid may encode a mutein lacking a signal sequence, and may consist of 159 streptavidin residues. The encoded mutein may have the sequence of SEQ ID NO:3. The nucleic acid may encode a mutein comprising a signal sequence, and may consist of 188 streptavidin residues. The encoded mutein may have the sequence of SEQ ID NO:5. The nucleic acid may encode a mutein further comprising a non-streptavidin sequence fused to said mutein, such as a cellulose binding domain, a chitin binding domain, a dextran binding domain, a silica binding peptide, a gold binding peptide or ferritin. The nucleic acid may be codon-modified, such as for expression in *Escherichia coli*, *Pichia pastoris*, *Saccharomyces cervesiae* or *Bacillus subtitils*. The nucleic acid may exhibit 80% homology to SEQ ID NO: 3, 90% homology to SEQ ID NO: 3 or 95% homology to SEQ ID NO: 3.

In yet another embodiment, there is provided a method of binding a biotin molecule comprising contacting a biotin molecule with a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine. The biotin molecule may bound to a matrix or support, or bound to a free biomolecule, such as a protein, a glycoprotein, a peptide, an oligonucleotide, a polynucleotide, a carbohydrate, a lipid, a glycolipid or a combination of any of the foregoing. The method may further comprise the step of reversing the binding of said biotin molecule and said complex. The mutein may further comprise a serine to alanine substitution at residue 27. The mutein may lack a signal sequence, and may mutein consist of 159 streptavidin residues. The mutein may have the sequence of SEQ ID NO:3. The mutein may further encode a non-streptavidin sequence fused to said mutein.

In still yet another embodiment, there is provided a method of binding a streptavidin binding peptide (SBP) comprising contacting a SBP molecule with a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine. The SBP molecule may be bound to a matrix, or to a free biomolecule, such as a protein, a glycoprotein, a peptide, an oligonucleotide, a polynucleotide, a carbohydrate, a lipid, a glycolipid or a combination of any of the foregoing. The method may further comprise the step of reversing the binding of said SBP molecule and said mutein.

In a further embodiment, there is provided a method of purifying a biotin- or SBP-tagged protein from a mixture comprising (a) providing a protein mixture comprising a biotin- or SBP-tagged protein; (b) contacting said protein mixture with a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine; and (c) separating said a biotin- or SBP-tagged protein bound to said streptavidin mutein. The method may further comprise releasing said biotin- or SBP-tagged protein from said streptavidin mutein. The mutein may be bound to a matrix or support, and the method may further comprise washing the matrix or support following step (b) and prior to step (c). The mutein may further comprise a serine to alanine substitution at residue 27. The mutein may lack a signal sequence, and the mutein may consist of 159 streptavidin residues. The mutein may have the sequence of SEQ ID NO:3. The mutein may further comprise a non-streptavidin sequence fused to said mutein. The mixture may be a cell lysate.

An additional embodiment includes a method of binding a biotin- or SBP-tagged protein to a solid matrix or support comprising (a) providing a biotin- or SBP-tagged protein; and (b) contacting said protein with a solid matrix or support onto which a streptavidin mutein comprising a substitution of the glycine at residue 48 corresponding to full-length wild-type streptavidin (SEQ ID NO:1), wherein said substitution comprises threonine, aspartic acid, glutamic acid, asparagines and glutamine is disposed. The mutein may further comprise a serine to alanine substitution at residue 27. The mutein may lack a signal sequence, and may consist of 159 streptavidin residues. The mutein may have the sequence of SEQ ID NO:3.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIGS. 1B-C) A single subunit in tetrameric streptavidin binds biotin and SBP tag, respectively. (FIG. 1D) Superimposition of the structures shown in FIGS. 1B-C. Both the S27 and G48 residues in these structures are shown. (FIG. 1E) Binding of the N-terminal SBP tag (lighter structure below and right of label B) in the A subunit of a tetrameric streptavidin. The entire SBP tag is shown in the space filled model. S27 and G48 in streptavidin and H12 and V14 in the N-terminal SBP tag are labeled. Only S27 (but not G48) makes close contacts with H12 and V14. The subunits of the tetrameric streptavidin protein are colored as specified in FIG. 1A. (FIG. 1F) Binding of the C-terminal SBP tag (intermediate shade under and to the right of label C) in the D subunit. Both S27 and G48 do not make any close contact with the C-terminal SBP tag.

FIGS. 4A-C. Purification of SBP tagged or biotinylated protein using SBPM18 Affigel. Purification of β-lactamase-SBP from culture supernatant under the column non-overloaded (FIG. 4A) and overloaded conditions (FIG. 4B), respectively. Purification of biotinylated maltose binding protein from a crude sample is shown in FIG. 4C. M: molecular weight markers; CS: culture supernatant containing secreted β-lactamase-SBP; S: crude sample containing biotinylated maltose binding protein; FT: flow-through fraction; W: wash fraction and E: elution fraction. The positions of β-lactamase-SBP and biotinylated maltose binding protein are marked by arrowheads.

DESCRIPTION OF ILLUSTRATIVE EMBODIMENTS

Figure 1:
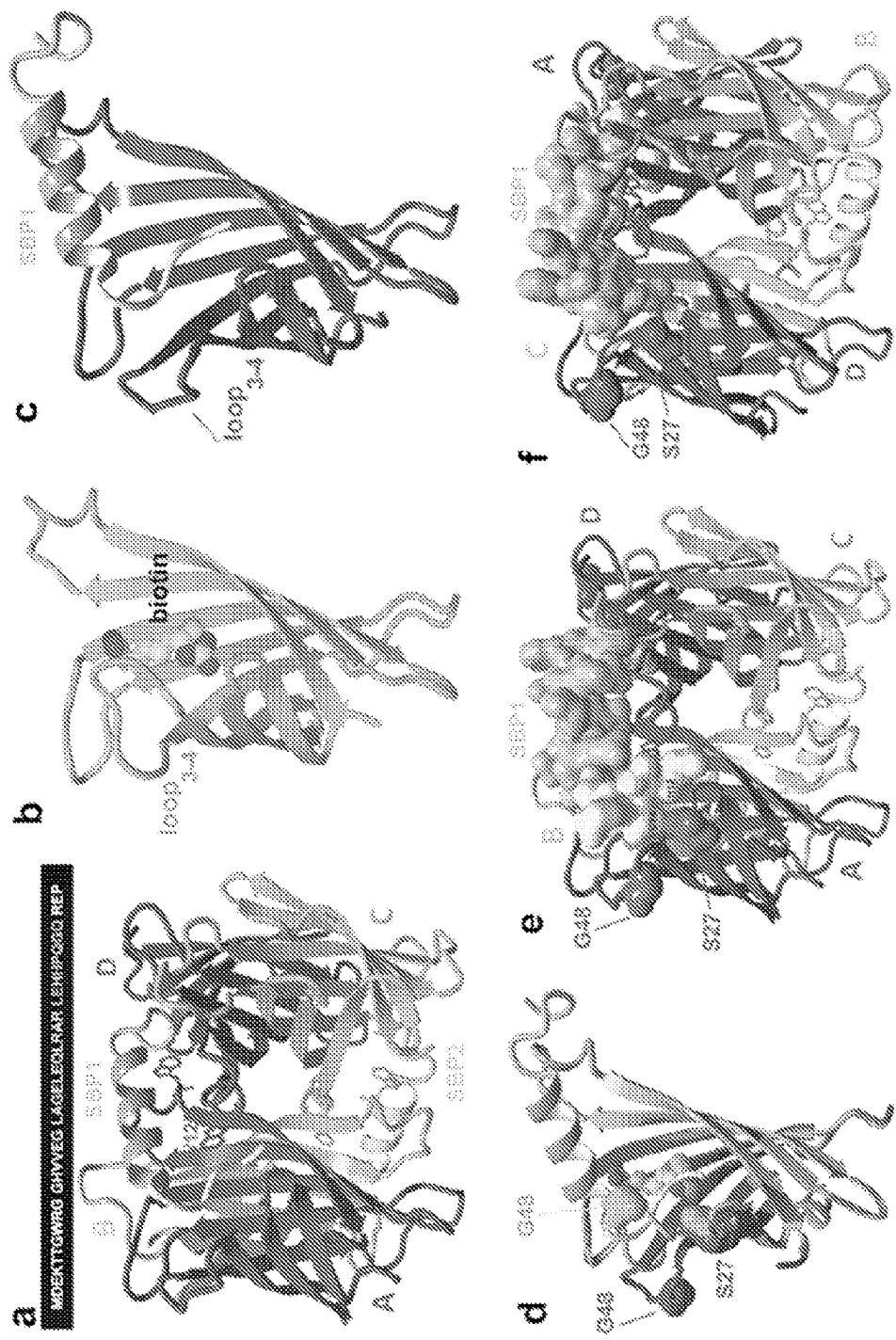
FIGS. 1A-F. Interactions between SBP tags and streptavidin (FIG. 1A) Sequence of the 38 amino-acid SBP tag (SEQ ID NO: 14) and the streptavidin-SBP complex. The SBP sequences in white are not visible in the streptavidin-SBP tag complex. The N- and C-terminal residues involved in binding to the SBP tag binding pocket in streptavidin are colored in yellow and greenish blue. The spacer sequence linking both the N- and C-terminal streptavidin binding peptides is shown in brown color. One tetrameric streptavidin can bind two SBP tags. The four streptavidin subunits are shown in different shades with the label adjadent—A subunit, B subunit, C subunit and D subunit. A complete SBP binding pocket in the A subunit requires Trp-120 from the D subunit. Trp-120 residue in the each subunit is illustrated.

In studies described below, the inventors have developed a new engineered streptavidin mutein, designated SBPM18, that can be produced via secretion from *Bacillus subtilis*. This tetrameric streptavidin retains high binding affinity to the SBP tag but has reversible biotin binding capability. The SBPM18 matrix can be applied to affinity purify SBP-tagged proteins or biotinylated molecules to homogeneity with high recovery in a reusable manner. A mild washing step is sufficient to regenerate the matrix which can be reused for multiple rounds. Recovery of SBP-tagged or biotinylated proteins can be 90%. These and other aspects of the invention are set forth in detail below.

1. Streptavidin and Biotin

A. Steptavidin

Streptavidin is a 52,800 dalton tetrameric protein purified from the bacterium *Streptomyces avidinii*. It has an extraordinarily high affinity for biotin (also known as vitamin B7); the dissociation constant ($K_d$) of the biotin-streptavidin complex is on the order of $\approx 10^{-14}$ mol/L, making it one of the strongest non-covalent interactions known in nature. Streptavidin is used extensively in molecular biology and bionanotechnology due to the streptavidin-biotin complex's resistance to organic solvents, denaturants (e.g., guanidinium chloride), detergents (e.g., SDS, Triton), proteolytic enzymes, and extremes of temperature and pH. The sequence for wild-type streptavidin is provided in SEQ ID NO:1.

The crystal structure of streptavidin with biotin bound was first solved in 1989. The N and C termini of the 159 residue full-length protein are processed to give a shorter 'core' streptavidin, usually composed of residues 13-139; removal of the N and C termini is not necessary for the high biotin-binding affinity. The secondary structure of a streptavidin monomer is composed of eight antiparallel β-strands, which fold to give an antiparallel beta-barrel tertiary structure. A biotin binding-site is located at one end of each β-barrel. Four identical streptavidin monomers (i.e., four identical β-barrels) associate to give streptavidin's tetrameric quaternary structure. The biotin binding-site in each barrel consists of residues from the interior of the barrel, together with a conserved Trp120 from neighbouring subunit. In this way, each subunit contributes to the binding site on the neighbouring subunit, and so the tetramer can also be considered a dimer of functional dimers.

The numerous crystal structures of the streptavidin-biotin complex have shed light on the origins of the remarkable affinity. Firstly, there is high shape complementarity between the binding pocket and biotin. Secondly, there is an extensive network of hydrogen bonds formed to biotin when in the binding site. There are eight hydrogen bonds directly made to residues in the binding site (the so called 'first shell' of hydrogen bonding), involving residues Asn23, Tyr43, Ser27, Ser45, Asn49, Ser88, Thr90 and Asp128. There is also a 'second shell' of hydrogen bonding involving residues that interact with the first shell residues. However, the streptavidin-biotin affinity exceeds that which would be predicted from the hydrogen bonding interactions alone, alluding to another mechanism contributing to the high affinity. The biotin-binding pocket is hydrophobic, and there are numerous van der Waals contacts and hydrophobic interactions made to the biotin when in the pocket, which is also thought to account for the high affinity. In particular, the pocket is lined with conserved tryptophan residues. Lastly, biotin binding is accompanied by the stabilisation of a flexible loop connecting β strands 3 and 4 (L3/4), which closes over the bound biotin, acting like a 'lid' over the binding pocket and contributing to the extremely slow biotin dissociation rate.

Most attempts at mutating streptavidin result in a lowered biotin-binding affinity, which is to be expected in such a highly optimised system. However, a recently engineered mutant of streptavidin, named traptavidin, was found to have more than ten-fold slower biotin dissociation, in addition to higher thermal and mechanical stability. This decreased dissociation rate was accompanied by a two-fold decrease in the association rate.

Among the most common uses are the purification or detection of various biomolecules. The strong streptavidin-biotin bond can be used to attach various biomolecules to one another or onto a solid support. A further application is the so called Strep-tag, which is an optimized system for the purification and detection of proteins. Streptavidin is widely used in Western blotting and immunoassays conjugated to some reporter molecule, such as horseradish peroxidase.

Streptavidin is a tetramer and each subunit binds biotin with equal affinity. Multivalency is an advantage in some applications, for example where avidity effects improve the ability of molecules attached to streptavidin to detect specific T cells. In other cases, such as the use of streptavidin for imaging specific proteins on cells, multivalency can perturb the function of the protein of interest. Monovalent streptavidin is an engineered recombinant form of streptavidin which is a tetramer but only one of the four binding sites is functional. This single binding site has $10^{-14}$ mol/L affinity and cannot cause cross-linking. In contrast, monomeric streptavidin is a recombinant form of streptavidin with mutations to break the tetramer into a monomer and to enhance the solubility of the resultant isolated subunit. Monomeric streptavidin has an affinity for biotin of $10^{-7}$ mol/L and so is not ideal for labeling applications but is useful for purification, where reversibility is desirable.

Streptavidin is not the only protein capable of binding to biotin with high affinity. Avidin is the other most notable biotin-binding protein, which is evolutionarily unrelated to streptavidin but has very similar properties. Originally isolated from egg white, avidin only has 30% sequence identity to streptavidin, but almost identical secondary, tertiary and quaternary structure. It has a higher affinity for biotin ($K_d \sim 10^{-15}$M), but in contrast to streptavidin, it is glycosylated, positively charged, has pseudo-catalytic activity (it can enhance the alkaline hydrolysis of an ester linkage between biotin and a nitrophenyl group) and has a higher tendency for aggregation. Also, streptavidin is the better biotin-conjugate binder; avidin has a lower binding affinity than streptavidin when biotin is conjugated to another molecule, despite avidin having the higher affinity for free, unconjugated biotin.

Streptavidin has a mildly acidic isoelectric point (pI) of ~5, but a recombinant form of streptavidin with a near-neutral pI is also commercially available Because streptavidin lacks any carbohydrate modification and has a near-neutral pI, it has the advantage of much lower nonspecific binding than avidin. Deglycosylated avidin (NeutrAvidin) is more comparable to the size, pI and nonspecific binding of streptavidin.

B. Biotin

As discussed above, biotin is a water-soluble B-complex vitamin (vitamin B7). It was discovered by Bateman in 1916 and is composed of a ureido (tetrahydroimidizalone) ring fused with a tetrahydrothiophene ring. A valeric acid substituent is attached to one of the carbon atoms of the tetrahydrothiophene ring. Biotin is a coenzyme in the metabolism of fatty acids and leucine, and it plays a role in gluconeogenesis.

Biotin is necessary for cell growth, the production of fatty acids, and the metabolism of fats and amino acids. It plays a role in the citric acid cycle, which is the process by which biochemical energy is generated during aerobic respiration. Biotin not only assists in various metabolic reactions but also helps to transfer carbon dioxide. Biotin may also be helpful in maintaining a steady blood sugar level. Biotin is often recommended for strengthening hair and nails. As a consequence, it is found in many cosmetics and health products for the hair and skin, though it cannot be absorbed through the hair or skin itself. Biotin deficiency is rare because, in general, intestinal bacteria produce biotin in excess of the body's daily requirements.

The empirical formula of biotin is $C_1H_{16}O_3N_2S$. Biotin has an unusual structure. It has two side rings fused together. The two side rings are imidazole and thiophene. Biotin is a heterocyclic S-containing monocarboxilic acid. Biotin D(+) is a cofactor responsible for carbon dioxide transfer in several carboxylase enzymes: Acetyl-CoA carboxylase alpha, Acetyl-CoA carboxylase beta, Methylcrotonyl-CoA carboxylase, Propionyl-CoA carboxylase and Pyruvate carboxylase. Thus, it is important in fatty acid synthesis, branched-chain amino acid catabolism, and gluconeogenesis. Biotin covalently attaches to the epsilon-amino group of specific lysine residues in these carboxylases. This biotinylation reaction requires ATP and is catalyzed by holocarboxylase synthetase. The attachment of biotin to various chemical sites can be used as an important laboratory technique to study various processes including protein localization, protein interactions, DNA transcription, and replication. Biotinidase itself is known to be able to biotinylate histone proteins, but little biotin is found naturally attached to chromatin.

Biotin binds very tightly to the tetrameric proteins avidin, streptavidin and neutravidin with a dissociation constant $K_d$ in the order of $10^{-15}$ M, which is one of the strongest known protein-ligand interactions, approaching the covalent bond in strength. This is often used in different biotechnological applications. Until 2005, very harsh conditions were required to break the biotin-streptavidin bond.

Biotin is consumed from a wide range of food sources in the diet, however there are few particularly rich sources. Foods with a relatively high biotin content include raw egg yolk (however, the consumption of egg whites with egg yolks minimizes the effectiveness of egg yolk's biotin in one's body), liver, some vegetables and peanuts. The dietary biotin intake in Western populations has been estimated to be 35 to 70 μg/d (143-287 nmol/d). Biotin is also available from supplements. The synthetic process developed by Sternbach and Goldberg in the 1940's uses fumaric acid as a starting material and is identical to the natural product.

Studies on the bioavailability of biotin have been conducted in rats and in chicks. From these studies, it was concluded that biotin bioavailability may be low or variable, depending on the type of food being consumed. In general, biotin exists in food as protein bound form or biocytin. Proteolysis by protease is required prior to absorption. This process assists free biotin release from biocytin and protein-bound biotin. The biotin present in corn is readily available; however, most grains have about a 20-40% bioavailability of biotin.

A possible explanation for the wide variability in biotin bioavailability is that it is due to ability of an organism to break various biotin-protein bonds from food. Whether an organism has an enzyme with the ability to break that bond will determine the bioavailability of biotin from the foodstuff.

As mentioned above, biotin is used experimentally by chemically linking it to proteins for biochemical assays. Its small size means the biological activity of the protein will most likely be unaffected. This process is called biotinylation. Because both streptavidin and avidin bind biotin with high affinity ($K_d$ of $\sim 10^{-14}$ mol/L) and specificity, biotinylated proteins of interest can be isolated from a sample by exploiting this highly-stable interaction. The sample is incubated with streptavidin/avidin beads, allowing capture of the biotinylated protein of interest. Any other proteins binding to the biotinylated molecule will also stay with the bead and all other unbound proteins can be washed away. However, due to the extremely strong streptavidin-biotin interaction, very harsh conditions are needed to elute the biotinylated protein from the beads (typically 6M GuHCl at pH 1.5), which often will denature the protein of interest. To circumvent this problem, beads conjugated to monomeric avidin can be used, which has a decreased biotin-binding affinity of $\sim 10^{-8}$ mol/L, allowing the biotinylated protein of interest to be eluted with excess free biotin. ELISAs often make use of biotinylated primary antibodies against the antigen of interest, followed by a detection step using streptavidin conjugated to a reporter molecule, such as horseradish peroxidase.

C. Streptavidin Binding Peptide

Keefe et al. (2001) were the first to describe a streptavidin-binding peptide (SBP) for both the one-step purification and the detection of recombinant proteins. The SBP-tag sequence is 38 amino acids long and binds to streptavidin with an equilibrium dissociation constant of 2.5 nM. The authors demonstrated that a single-step purification of SBP-tagged proteins from bacterial extract yields samples that are more pure than those purified using maltose-binding protein or the His-tag. The capacity of the immobilized streptavidin used to purify SBP-tagged proteins is about 0.5 mg per milliliter of matrix, which is high enough to isolate large quantities of proteins for further study. Also, the elution conditions from the streptavidin column are very mild and specific, consisting of the wash buffer plus biotin. This combination of high-affinity, high-yield, mild elution conditions, and simplicity of use makes the SBP-tag suitable for high-throughput protein

D. Steptavidin Muteins

In accordance with the present invention, the inventor has provided modified streptavidin molecules. In particular, the inventor has created a single mutant containing a single mutation of serine to alanine substitution at residue 27, and a double mutant containing tht change as well as a glycine to threonine substitution at residue 48 corresponding to full-length wild-type streptavidin (SEQ ID NO:1). Although threonine is exemplified as a replacement residue for glycine 48, other residues with bulky side chains and high propensity for turns ($P_t$>0.83) are contemplated (e.g., Asp, Glu, Asn, Gln). $P_t$ is calculated from the fraction of residues of each amino acid that occurred in the turn conformation, divided by this fraction of all residues.

While it is envisioned that the aforementioned changes may be made in the wild-type sequence, other variation in non-critical regions of the molecule may be made. Such variation would typically be conservative substitutional mutations. Substitutional mutations involve the exchange of one amino acid for another at one or more sites within the protein, and may be designed to modulate one or more properties of the polypeptide, such as stability against proteolytic cleavage, without the loss of other functions or properties. Conservative substitutions, that is, one amino acid replaced with one of similar shape and charge, are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of streptavidin muteins, but with altered and even improved characteristics.

The present invention may employ peptides that comprise modified, non-natural and/or unusual amino acids. A table of exemplary, but not limiting, modified, non-natural and/or unusual amino acids is provided herein below. Chemical synthesis may be employed to incorporated such amino acids into the peptides of interest.

TABLE 1

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

E. Purification of Proteins

It may be desirable to purify proteins according to the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein. The term "purified protein" as used herein, is intended to refer to a composition, isolatable from other components, wherein the protein is purified to any degree relative to its naturally-obtainable state. A purified protein therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. The clear example for the present invention is the use of biotin as the ligand.

2. Nucleic Acids

Important aspects of the present invention concern isolated DNA segments and recombinant vectors encoding streptavidin muteins and portions thereof, the creation and use of recombinant host cells through the application of DNA technology, that express steptavidin muteins. Sequences for steptavidin and the mutein nucleic acids include SEQ ID NOS:1 and 3, respectively.

The present invention concerns DNA segments, isolatable from bacterial cells that are free from total genomic DNA and that encode steptavidin muteins. As used herein, the term "DNA segment" refers to a DNA molecule that has been isolated free of total genomic DNA of a particular species. Therefore, a DNA segment encoding steptavidin muteins refers to a DNA segment that is isolated away from, or purified free from, total mammalian genomic DNA. Included within the term "DNA segment" including DNA segments such recombinant vectors, including, for example, plasmids, cosmids, phage, viruses, and the like.

In particular embodiments, the invention concerns isolated DNA segments and recombinant vectors incorporating DNA sequences that encode steptavidin muteins. The term "biologically functional equivalent" is well understood in the art and is further defined in detail herein. Accordingly, nucleic acid sequences that have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 75% to about 99%, and more particularly about 81% and about 99% or about 86% to about 99%; or even more particularly, between about 91% and about 99%; of amino acids that are identical or functionally equivalent to the amino acids of, for example, SEQ ID NO:1, SEQ ID NO: 3, SEQ ID NO: 5, SEQ ID NO: 7, or SEQ ID NO: 9. In particular embodiments, the biological activity of a steptavidin muteins comprises stable low affinity binding to biotin, including reversible binding. "Stable low affinity binding" may include a dissociation constant ($K_D$) for biotin of the mutein in the range of $10^{-7}$ to $10^{-8}$M, and/or and an off-rate ($k_{off}$) for bound biotin in the streptavidin-biotin complex at about $10^{-4}$ sec$^{-1}$.

Another way of defining homology for nucleic acids is by hybridization conditions. For example, a nucleic acid will hybridize to sequences of greater or less homology based on the stringency of the hybridization conditions. For example, high stringency conditions may be exemplified by those including approximately 10 mM Tris-HCl (pH 8.3), 50 mM KCl, 1.5 µM MgCl$_2$, at temperatures ranging from approximately 40° C. to about 72° C. A specific example of stringent hybridization conditions is overnight incubation at 42° C. in a solution comprising: 50% formamide, 5.times.SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., (1989), particularly Chapter 11 therein. Solution hybridization may also be used with the polynucleotide sequences provided by the invention.

It will also be understood that nucleic acid sequences may include those that encode additional residues, such as 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Obtaining Nucleic Acid Sequences

There are several methods available and well known to those skilled in the art to obtain DNAs encoding proteins. Sequences may be produced using PCR™ (or RT-PCR) (see U.S. Pat. No. 4,683,202, U.S. Pat. No. 5,928,906, each incorporated herein by reference). Alternatively the method of Rapid Amplification of cDNA ends (RACE) (see, for example, Frohman et al., 1988) may be used, including modifications of the technique, exemplified by the Marathon® technology (Clontech Laboratories Inc.). In Marathon®, cDNAs have been prepared from mRNA extracted from a chosen tissue and an 'adaptor' sequence ligated onto each end. PCR is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

4. Engineering Cells to Express Steptavidin Muteins

In certain embodiments, the present invention involves the production of streptavidin muteins. Such methods both rely upon expression constructs containing a streptavidin mutein coding region and the means for its expression, plus elements that permit replication of the constructs. Expression requires that appropriate signals be provided in the vectors, and which include various regulatory elements that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Vectors

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression.

B. Host Cells

While a variety of host cells can be used in accordance with the present invention, a particularly useful host cell is the bacterium *Bacillus subtilis*. Known also as the hay *bacillus* or grass *bacillus*, *B. subtilis* is a Gram-positive, catalase-positive bacterium commonly found in soil. A member of the genus *Bacillus*, *B. subtilis* is rod-shaped, and has the ability to form a tough, protective endospore, allowing the organism to tolerate extreme environmental conditions. Unlike several other well-known species, *B. subtilis* has historically been classified as an obligate aerobe, though recent research has demonstrated that this is not strictly correct.

*B. subtilis* is not a human pathogen. It may contaminate food but rarely causes food poisoning. *B. subtilis* produces the proteolytic enzyme subtilisin. *B. subtilis* spores can survive the extreme heat during cooking. It can divide symmetrically to make two daughter cells (binary fission), or asymmetrically, producing a single endospore that is resistant to environmental factors such as heat, acid, and salt, and which can persist in the environment for long periods of time. The endospore is formed at times of nutritional stress, allowing the organism to persist in the environment until conditions become favorable. Prior to the process to produce the spore the bacterium might become motile, through the production of flagella, and also take up DNA from the environment.

*B. subtilis* is a model organism used to study bacterial chromosome replication. Replication of the single circular chromosome initiates at a single locus, the origin (oriC). Replication proceeds bidirectionally and two replication forks progress in clockwise and counterclockwise directions along the chromosome. Chromosome replication is completed when the forks reach the terminus region, which is positioned opposite to the origin on the chromosome map. The terminus region contains several short DNA sequences (Ter sites) that promote replication arrest. Specific proteins mediate all the steps in DNA replication. Comparison between the proteins involved in chromosomal DNA replication in *B. subtilis* and in *Escherichia coli* reveals similarities and differences. Although the basic components promoting initiation, elongation, and termination of replication are well-conserved, some important differences can be found (such as one bacterium missing proteins essential in the other). These differences underline the diversity in the mechanisms and strategies that various bacterial species have adopted to carry out the duplication of their genomes.

*B. subtilis* has proven highly amenable to genetic manipulation, and has become widely adopted as a model organism for laboratory studies, especially of sporulation, which is a simplified example of cellular differentiation. It is also heavily flagellated, which gives *B. subtilis* the ability to move quite quickly. In terms of popularity as a laboratory model organism, *B. subtilis* is often used as the Gram-positive equivalent of *E. coli*. *B. subtilis* is capable of secreting some extracellular proteins to high levels and extracellular protease deficient strains have been developed to stabilize the secreted proteins (Wu et al., 2002)

5. Definitions

The word "about" means plus or minus 5% of the stated number.

As used herein, "affinity" refers to the dissociation constant ($K_d$) of a complex between a mutein or streptavidin, and biotin, as determined by standard methods known to those skilled in the art, an example of which is disclosed in the Examples herein. As is known in the art, $K_d$ is related to the association constant $K_a$, being the inverse thereof.

As used herein, "lower binding affinity" means a decrease in the binding affinity relative to streptavidin, which can be measured as an increase in $K_d$ or, alternatively, a decrease in $K_a$. The lower binding affinity can result from a change in one or both of $k_{on}$ (the "on rate," or "association rate constant," or $k_a$) and $k_{off}$ (the "off rate," or "dissociation rate constant," or $k_d$).

As used herein, "monomeric form" or "monomer" means a streptavidin or mutein subunit that is not in the form of a complex with another streptavidin or mutein subunit, or that does not form a complex with another streptavidin or mutein subunit.

As used herein, "tetrameric form" or "tetramer" means a protein complex that is comprised of four streptavidin and/or mutein subunits, and includes complexes in which one or more of the four subunits are different from one another.

As used herein, "subunit" means the protein that is generated from a streptavidin or mutein gene. "Subunit" is used interchangeably with "monomer."

6. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Construction of pSAVSBPM18.

The synthetic gene encoding the SBPM18 version of streptavidin was ordered from Epoch Biolabs Inc. (Texas, USA). This gene was in an *E. coli* bluescript vector (pBSK-SBPM18). The plasmid was digested by PstI and BclI to release a DNA fragment encoding SBPM18. This 442-bp fragment was inserted to the PstI and BclI digested pSSAV (Perbandt etr al., 2007) to generate pSAVSBPM18. In this plasmid, P43, a strong and constitutively expressed promoter, directs the transcription. The *B. subtilis* levansucrase (sacB) signal peptide is applied for secretion.

Production and Purification of SBPM18.

SBPM18 mutein was produced by *B. subtilis* WB800 [pSAVSBPM18] cultured for 14-16 hours at 30° C. in a defined medium (Wu and Wong, 2002). The culture supernatant containing secreted proteins was concentrated using ultrafiltration and dialyzed in physiological buffered saline (PBS, 0.1M sodium phosphate, 0.15M sodium chloride, pH 7.5). SBPM18 was purified on a biotin-agarose (Sigma, Canada) column. After loading sample on the column, the column was washed with 5-6 column volumes of PBS. Bound proteins were eluted by PBS containing 5 mM d-biotin. Fractions containing pure SBPM18 were pooled, concentrated and dialyzed against PBS. Purified SBPM18 was quantified spectrophotometrically at 280 nm using a molar extinction coefficient of 41,940 $M^{-1}$ $cm^{-1}$.

Purification of β-Lactamase-SBP Using Immobilized SBPM18 and Wild-Type Streptavidin-Agarose.

Pure SBPM18 was immobilized on Affi-gel 15 (BioRad, Canada). The coupling procedure and quantitation of the amount of SBPM18 coupled were according to the manufacturer's instructions. The crude sample containing β-lactamase-SBP was the culture supernatant of WB800[pWB980-β-lactamase-SBP] cultured in a defined medium (Wu and Wong, 2002). After washing the column with PBS, bound β-lactamase-SBP was eluted from the column using PBS containing 5 mM d-biotin. The column was regenerated by washing with ten column volumes of PBS. The wild-type streptavidin-agarose matrix (S1638) from Sigma Canada was used.

Purification of Biotinylated MBP Using Immobilized SBPM18.

A crude sample containing the soluble fraction of *E. coli* cell extract and pure biotinylated maltose binding protein (MBP-AviTag fusion, Avidity, LLC, USA) was loaded onto SBPM18 matrix. The column was washed by PBS and the bound protein was eluted by PBS containing 5 mM d-biotin. The column was regenerated by washing with ten column volumes of PBS.

Kinetic Analysis of SBPM18 Streptavidin Mutein.

The kinetic parameters (on- and off-rates for interaction with biotin; on- and off-rates for interaction with SBP tag) of SBPM18 were determined in real time using the surface plasmon resonance-based BIA-coreX biosensor (GE Healthcare, Canada) as described previously (Wu and Wong, 2005b). For the study on biotin interaction, biotinylated MBP-AviTag (Avidity, LLC) was used as the ligand. For the study on SBP interaction, two different ligands were used. The first is a synthetic peptide from Peptide 2.0 Inc. (VA., USA). It is a 59-amino acid peptide which comprises the full length SBP tag (highlighted in bold) with the sequence:

(SEQ ID NO: 10)
CGGGGSTSGGSTSGGSTSGGGMDEKTTGWRGGHVVEGLA

GELEQLRARLEHHPQGQREP

The cysteine residue at the N-terminus is designed for thiol coupling of the peptide to the BIAcore biosensor CMS chip. A 20-amino acid glycine-rich linker is present between the N-terminal cysteine residue and the SBP tag to project the tag to the chip surface. The second ligand is β-lactamase-SBP purified on the SBPM18 matrix. This protein was coupled to the CMS sensor chip via the amine coupling approach. All the coupling procedures (thiol and amine coupling) were performed according to the manufacturer's instructions. A blank flow cell was used as the reference cell in all studies.

Characterization of SBPM18 Using SEC-MALS.

The molar mass and molecular size distributions of SBPM18 were determined by multi-angle light scattering (MALS) detection system used in conjunction with size exclusion chromatography (SEC). Pure sample of SBPM18 was fractionated on a size exclusion column (TSK-GEL SuperSW2000, Tosoh Bioscience, USA) using a Shimadzu Prominence HPLC system which is equipped with a column temperature control oven (Shimadzu Prominence CTO-20AC Column Temperature Oven) to control the temperature of both the injector and column. The light scattering instrumentation consists of a multiangle, static light scattering detector (DAWN-HELEOS II from Wyatt Technology Corp., USA) interfaced with a dynamic light scattering detector (WyattQELS) and an online concentration detector (Wyatt Optilab rEX differential refractometer). Absolute molar mass, molecular size and fraction distributions of SBPM18 were analyzed using ASTRA V software (Wyatt Technology Corp., USA).

Analysis of Interactions Between SBP Tag and Streptavidin Using Molegro Viewer.

The pdb file of the streptavidin-SBP tag complex was used as the input file. In this file, one of the SBP tags in the complex was labelled as ligand. The file was imported to Molegro Molecular Viewer (Version 2.2.0) (Thomsen and Christensen, 2006). Interaction energy analysis was performed using the ligand energy inspector module in the program. Before analysis, both the ligand and protein hydrogen bonding positions were optimized and the ligand was energy minimized using the action panel in the ligand energy inspector module. The protein-ligand interaction energy ($E_{inter}$, sum of the steric interaction energy, hydrogen bonding energy, short- and long-range electrostatic interaction energies) was expressed in the form of the MolDock score (Thomsen and Christensen, 2006) in arbitrary units. The more negative the value reflects a stronger interaction. The graphic drawings of the structure of the SBP-SBPM18 complex shown in FIGS. 1A-F were generated by using both the Swiss-pdb viewer (Guex and Peitsch, 1997) and Yasara (Krieger et al., 2002) (YASARA Biosciences GmbH, Austria) programs.

Example 2

Results

Rational Design of Streptavidin SBPM18.

The mechanism for the SBP tag to have a tight binding to streptavidin has been examined by determining the structure of the SBP-streptavidin complex via X-ray crystallography (manuscript in preparation). Interestingly, only 25 amino acids (colored residues) in the full-length SBP tag are required for tight binding (FIG. 1A). This 25-amino-acid sequence (SEQ ID NO:15) can be divided into three functional segments. The first six amino acids (GHVVEG (SEQ ID NO:11)) and the last seven amino acids (LEHHPQGQ (SEQ ID NO:12)) from the tag form two binding segments. Each segment binds to a binding pocket formed by two different subunits in the tetrameric streptavidin. For the N-terminal binding segment, it binds to a binding pocket formed mainly by the A subunit. A Trp-120 residue from the C subunit is required to form a complete binding pocket (FIG. 1A). This residue is suggested to make major interactions with the peptide tag. Similarly, the C-terminal binding peptide binds to the binding pocket formed mainly by the C subunit. The Trp-120 residue from the A subunit is also required to form a complete binding pocket. The 11-amino-acid central segment (LAGELEQLRAR (SEQ ID NO: 13)) has dual functions. It forms a helical structure which functions as a spacer to allow the two binding segments to insert into the peptide binding pockets in streptavidin. At the same time, some of the residues also interact with streptavidin to strengthen the binding. To develop an engineered streptavidin (SBPM18) with high affinity to SBP but lower affinity to biotin, it is crucial to identify streptavidin residues that are only important for biotin binding but are not (or less) important for SBP binding for mutagenesis. Since the two streptavidin binding peptide segments from the SBP tag actually bind to the biotin binding pockets (FIGS. 1A-D), most of the streptavidin residues that are critical for biotin binding are also important for SBP binding. However, there is one major difference between the biotin binding and the SBP tag binding in streptavidin. The $loop_{3-4}$ which connects the β-strands 3 and 4 in streptavidin is in a closed configuration with biotin as the binding ligand (FIG. 1B) (Freitag et al., 1997). Three residues (Val-47, Gly-48 and Asn-49) in this loop make major contacts with biotin. In contrast, this loop is in an open configuration when streptavidin binds the SBP tag (FIG. 1C). Gly-48 in this loop interacts with biotin but is clearly not involved in SBP binding (FIG. 1D). Replacement of Gly-48 with Thr which has a bulkier side chain may affect the loop conformation so that this loop may not be able to make close contacts with biotin anymore. Since glycine is crucial to induce the turn formation in a loop, it is important for the replacement residue to have a high propensity for turn formation. Threonine meets this requirement.

The G48T streptavidin mutein designated SBPM12 was constructed and secretory produced from *B. subtilis*. This mutein retained almost full binding strength to the SBP tag (Table 2) but had a lower biotin binding affinity ($K_d$=4.45× $10^{-10}$M). Kinetic studies indicated that the drop in biotin binding affinity was mainly contributed by a significant increase (>$10^3$ times) in off-rate which is consistent with the prediction that the mutated $loop_{3-4}$ is no longer able to make good contact with the bound biotin to retain it in the biotin binding site. Although the drop in biotin binding affinity in SBPM12 is significant ($10^4$ times in reference to the wild-type streptavidin), it is not sufficient for SBPM12 to bind biotin in a reversible manner. One extra mutation would be needed to further reduce the biotin binding affinity. The interactions between the SBP tag and streptavidin was quantitatively predicted using the Molegro program (Thomsen and Christensen, 2006). Ser-27 was identified as an attractive candidate since it has only weak interactions with SBP (FIGS. 1D-F). In contrast, the S27A mutation (Klumb et al., 1998) has previously been shown to change the biotin dissociation constant from $10^{-14}$M to $10^{-12}$M. Therefore, SBPM12 was further modified to generate SBPM18 which has double mutations (S27A, G48T).

TABLE 2

Kinetic parameters for the interactions between streptavidin variants and the binding ligands

| | SBPM18 | | | wt SAV | | | SBPM12 | | |
|---|---|---|---|---|---|---|---|---|---|
| | On-rate ($m^{-1}s^{-1}$) | Off-rate ($s^{-1}$) | $K_d$ (M) | On-rate ($m^{-1}s^{-1}$) | Off-rate ($s^{-1}$) | $K_d$ (M) | On-rate ($m^{-1}s^{-1}$) | Off-rate ($s^{-1}$) | $K_d$ (M) |
| Biotinylated MBP | $2.30 \times 10^5$ | $2.65 \times 10^{-3}$ | $1.15 \times 10^{-8}$ | $5.13 \times 10^{6*}$ | $2 \times 10^{-7***}$ | $4 \times 10^{-14**}$ | $1.10 \times 10^6$ | $4.89 \times 10^{-4}$ | $4.45 \times 10^{-10}$ |
| SBP tag (peptide) | $1.07 \times 10^5$ | $8.21 \times 10^{-4}$ | $7.67 \times 10^{-9}$ | $3.00 \times 10^5$ | $4.96 \times 10^{-4}$ | $1.65 \times 10^{-9}$ | $2.81 \times 10^5$ | $5.60 \times 10^{-4}$ | $1.99 \times 10^{-9}$ |
| β-lactamase-SBP | $4.53 \times 10^4$ | $7.11 \times 10^{-4}$ | $1.57 \times 10^{-8}$ | $9.50 \times 10^4$ | $8.16 \times 10^{-4}$ | $8.59 \times 10^{-9}$ | ND | ND | ND |

*Value determined by the surface plasmon resonance method described in Qureshi and Wong (2002)
**Value from Green (1990).
***Value calculated based on the on-rate and $K_d$ shown in the table.
ND: Not determined.

Binding Properties of SBPM18.

Figure 2:
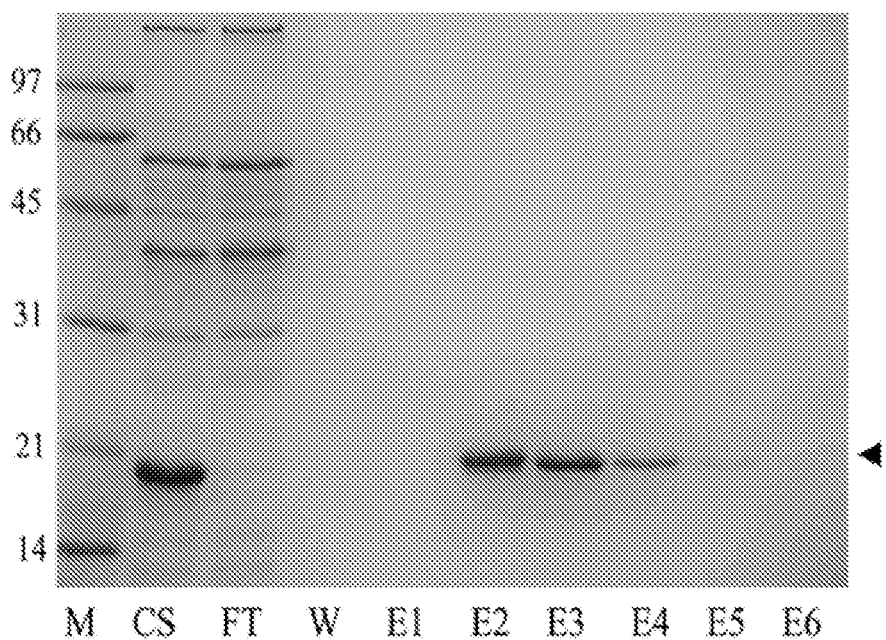
FIG. 2. Purification of SBPM18. Secreted SBPM18 produced from WB800[pSAVSBPM18] was affinity purified using biotin-agarose. Fractions were analyzed by SDS-PAGE. M: Molecular weight markers; CS: culture supernatant; FT: Flow-through fraction; W: wash fraction; E1-E6: elution fractions. Arrowhead marks the position of SBPM18.

Streptavidin SBPM18 was produced from *B. subtilis* via secretion in its functional form with a production yield of 7-12 mg/liter. The mutein was affinity purified to homogeneity using biotin-agarose (FIG. 2) with a recovery of 90%. Purified SBPM18 bound to the SBP tag immobilized on the sensor chip showed a dissociation constant ($7.67 \times 10^{-9}$M, Table 2) that is in the same order of magnitude as the wild-type streptavidin. To examine whether fusing the SBP tag to a protein affects its interaction with streptavidin, a β-lactamase-SBP fusion was constructed. This fusion has a 19 amino-acid linker as the spacer. With β-lactamase-SBP immobilized to the sensor chip for analysis, SBPM18 showed a slightly lower binding affinity ($1.57 \times 10^{-8}$M) which again is comparable with that of the wild-type streptavidin ($8.6 \times 10^{-9}$M). In terms of the biotin binding affinity, SBPM18 had a $K_d$ of $1.15 \times 10^{-8}$ M (Table 2). In fact, SBPM18 binds to β-lactamase-SBP and biotinylated maltose binding protein (MBP) with similar affinities. Biotin in excess should be an effective competitor to displace SBP off from SBPM18.

Tetrameric State of SBPM18.

Figure 3:
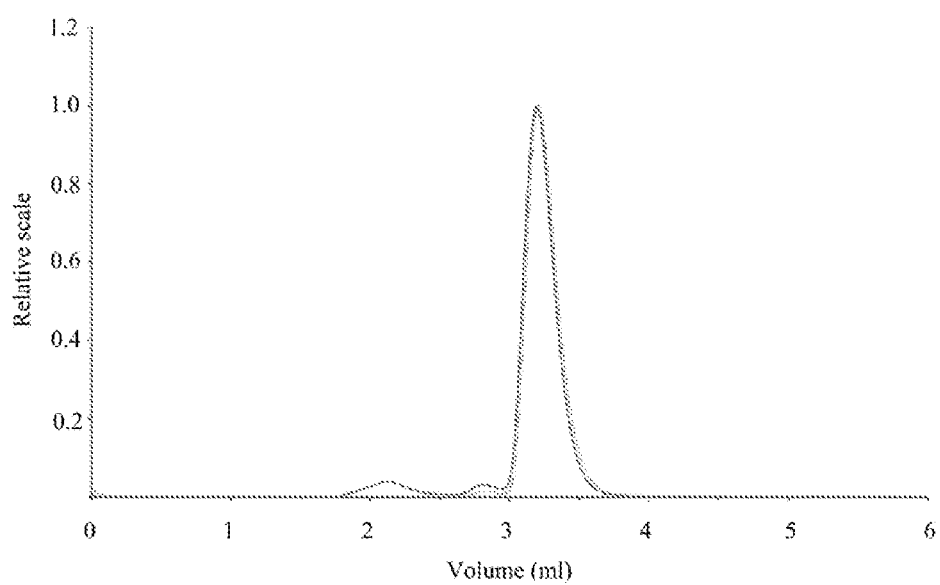
FIG. 3. Tetrameric state of SBPM18 analysed by HPLC size exclusion chromatography with in-line static and dynamic light scattering detectors, UV monitor and refractometer. Purified SBPM18 at room temperature in the absence of biotin was applied to a size-exclusion column. Solid line: elution profile monitored by the static light scattering detector. Dotted line: elution profile monitored by the UV detector. Of the two UV detectable peaks (elution volume~2.8 ml and 3.2 ml, respectively), the major peak (eluted around 3.2 ml) represents the tetrameric SBPM18 with a molecular mass of 65 kDa. The mass fraction of this peak is 99.3%.

Tetrameric state of streptavidin is vital for SBPM18 to have a tight binding of the SBP tag. The oligomeric state of SBPM18 in solution in the presence or absence of biotin at room temperature was analyzed using the high-performance size-exclusion chromatography combined with in-line dynamic and static light scattering detectors, refractometer and UV monitor (Harding and Jumel, 2001). In the absence of biotin, there was only a single major peak with a mass fraction of 99.3% in the chromatogram (FIG. 3). The polydispersity index of this peak was 1.007. This reflects that SBPM18 in this peak has a uniform size, shape and mass distribution. SBPM18 in this major peak showed a molecular mass of 64.5 kDa and a hydrodynamic radius of 3.2 nm. Since the expected molecular mass of the tetrameric SBPM18 is 66 kDa, this demonstrates that SBPM18 in solution is in the tetrameric state. No protein peaks corresponding to dimeric and monomeric SBPM18 subunits were detected. In the presence of biotin, a single protein peak with a mass fraction of 99% was observed in the chromatogram. The molecular mass of the SBPM18-biotin complex was determined to be 69.6 kDa with a polydispersity index of 1.013. To confirm the tetrameric nature of SBPM18 at a higher temperature, SBPM18 was placed in 40° C. water bath for 30 minutes and subsequently injected to the HPLC system with the temperature of both the injector and the column controlled at 40° C. The chromatogram once again showed a single peak of tetrameric SBPM18 with a mass fraction of 99% either in the presence or absence of biotin (data not shown). Since protein purification in general is performed at room temperature, SBPM18 which can maintain the tetrameric state at 40° C. should be stable enough for affinity purification of SBP-tagged or biotinylated proteins.

Application of SBPM18 to Purify SBP-Tagged β-Lactamase.

β-lactamase-SBP was used as a model protein for purification using both SBPM18-affigel and wild-type streptavidin-agarose matrices. Culture supernatants containing the secreted β-lactamase-SBP were loaded to these matrices under two different conditions from below the theoretical column binding capacity to overloading the column with excess β-lactamase-SBP. The theoretical column binding capacity expressed in terms of micrograms of β-lactamase-SBP that can bind to the matrix if all the SBP binding sites can be fully accessible was estimated based on the assumption that a streptavidin dimer can bind one β-lactamase-SBP. As shown in FIG. 4A and Table 3, under the non-overloaded condition (20% of the column binding capacity), β-lactamase-SBP could be affinity purified to high purity in one step with a recovery of 91% by using the SBPM18-affigel matrix. The recovery of β-lactamase-SBP using the wild-type streptavidin-agarose matrix also reached 88% (Table 3). In the second condition, the amounts of sample loaded exceeded the theoretical column capacity by 33-50%. Leakage of the bound β-lactamase-SBP from the SBPM18-affigel column under the washing condition was observed (FIG. 4B). It is important to note that besides the first two wash fractions which had contaminants, wash fractions 3-6 contained pure β-lactamase-SBP. Therefore, fractions 3-6 were pooled together with the elution fractions to increase the recovery. Analyses of the samples from the boiled matrix by SDS-PAGE and Western blot indicate that no β-lactamase-SBP could be detected as retention on the column after elution (data not shown). Leakage of β-lactamase-SBP under the wash condition was also observed with the wild-type streptavidin matrix. Under the column overloaded condition, the final recovery was 58% for the SBPM18 matrix and 37% for the wild-type streptavidin matrix. To regenerate the SBPM18 matrix for next cycle of purification, the column was simply washed the wash buffer. The SBPM18 matrix had been reused 8 times without any obvious loss in binding capacity.

TABLE 3

Purification of (β-lactamase-SBP using various streptavidin matrices

| Wild-type streptavidin | 1102 | 1650 | 150 | 953** | 58 |
|---|---|---|---|---|---|
| | 1008 | 202 | 20 | 178 | 88 |
| | 1008 | 1344 | 133 | 499** | 37 |

*Theoretical binding capacity is expressed in terms of the amounts (μg) of β-lactamase-SBP that can bind to the matrix. This value is estimated with the assumption that one SBP tag binds to two subunits in a tetrameric streptavidin. 1 μg of streptavidin dimer (Mr = 33,038) will bind 1.06 μg of β-lactamase-SBP (Mr = 35,030.6). New matrix was used in each binding study.
**Amount recovered is based on the total amount of pure proteins recovered in certain selected wash fractions and the elution fractions.

Application of SBPM18 to Purify Biotinylated Maltose Binding Protein.

SBPM18-affigel could be applied to purify biotinylated maltose binding protein effectively. Over 75% of the eluted maltose binding proteins were in the second and third elution fractions (FIG. 4C). The overall recovery was approximately 90%. No biotinylated MBP could be detected from the column matrix after elution. This matrix could be easily regenerated by washing the column with the wash buffer and had been reused at least 5 times without any detectable loss in binding capacity.

Example 3

Discussion

Rationale Behind the Design of SBPM18.

Because of the high affinity and specificity of the SBP tag to streptavidin, this system has been successfully applied for one-step affinity purification of proteins (Keefe et al., 2001; Kobayashi et al., 2008), protein complexes (Kim et al., 2010) and nano-particles (Xiao et al., 2009). It has also been applied to study protein-protein interactions (Kim et al., 2010; Li et al., 2011), remove nucleases to improve cell-free translation efficiency (Seki et al., 2009) and develop improved tandem tags for protein studies (Burckstummer et al., 2006). To make this powerful technology to be cost effective, development of an idealized streptavidin mutein, provided here as SBPM18, is essential. The key to the successful development of such a mutein relies on the ability to create this desirable mutein with minimal changes in the streptavidin sequence. Structural model suggests that the G48T mutation should not affect SBP tag binding but should reduce the biotin binding affinity (FIG. 1D). Characterization of SBPM12 indeed confirms this prediction (Table 2). Selecting S27A as the second mutation is to take advantage of the weak interactions between Ser-27 and the SBP tag, plus the reduced biotin binding ability introduced by the mutation. Since the sequences in the N- and C-terminal binding segments in the SBP tag are different, they interact with the binding pocket differently. Ser-27 in the A subunit of streptavidin only interacts weakly with His-12 and Val-14 in the N-terminal binding segment (FIG. 1E). The sum of the interaction energy scores for these residues (Ser-27 in SBPM18 with His-12 in the SBP tag and Ser-27 with Val-14) analyzed by the Molegro program corresponds to 0.8% of the total interaction energy score for one SBP tag to bind to streptavidin. Furthermore, Ser-27 in the C subunit of streptavidin has no interaction with the C-terminal binding segment in the SBP tag (FIG. 1F). The binding properties of SBPM18 reflect that the S27A mutation indeed does not significantly affect the SBP tag binding while further weakening biotin binding (Table 2). Another important reason to select G48T and S27A in streptavidin for mutagenesis is that these mutations are less likely to affect subunit interactions in streptavidin. These residues are not located at the subunit interface or in a loop structure (i.e., loop$_{7-8}$) that is involved in subunit interactions. Consequently, SBPM18 should have a stable tetrameric structure in solution as verified by the HPLC analysis.

A stable tetrameric structure is essential for tight SBP tag binding for three reasons. First, just like the biotin binding pocket, each complete SBP tag binding pocket required to bind a binding segment in a SBP tag is formed by two subunits (e.g., subunits A/C). Second, stable binding of a single SBP tag requires both the N- and C-terminal binding segments of the SBP tag to bind to two SBP tag binding pockets to gain the avidity effect. If SBPM18 dissociates into monomers, its ability to bind SBP tag will be greatly reduced. Even if SBPM18 dissociates into dimers, it will still have poor ability to bind the SBP tag because of the following reason. The natural tetrameric streptavidin is formed by dimerization of two dimers. Subunits A and B (or subunits C and D) have strong subunit interactions and spontaneously form A/B or C/D dimers. These dimers do not possess a complete SBP binding pockets as those formed by subunits A/C or subunits B/D. Third, to generate the affinity matrix, it is vital to have only one subunit in the streptavidin tetramer to be coupled to the matrix so that all the binding sites in the tetramer can be more readily accessible. This is particularly important for SBP tag binding since one tag has to interact with two subunits. If the other three subunits that are not covalently coupled to the matrix have a tendency to dissociate from the tetrameric streptavidin structure, leakage of streptavidin subunits from the matrix can be a problem.

Purification of SBP-Tagged β-Lactamase.

Although the development of the SBP tag has been around for 10 years, no systematic study of the streptavidin column capacity in relation to the binding behaviour of the SBP-tagged proteins has been made. As illustrated in this study, overloading the column could weaken the interaction between the SBP-tagged protein and streptavidin. Leakage of the SBP-tagged protein in the wash fractions was observed. When the SBP-tagged proteins are in excess during loading, one SBP tag is most likely to interact with one subunit instead of two subunits in the tetrameric streptavidin. Since either the N- or C-terminal streptavidin binding segment in a SBP tag is not strong enough to allow the SBP-tagged protein to bind tightly to streptavidin (Wilson et al., 2001), leakage of the bound SBP-tagged proteins can result. In this study, β-lactamase-SBP leaked out in most of the wash fractions is relatively pure. It can be combined with the purified protein in the elution fraction. Without overloading the column, the recovery of the SBP-tagged protein was in the range of 90% whether the wild-type streptavidin or SBPM18-affigel matrix was used. Under the overloaded condition, SBPM18-affigel matrix consistently offered better recovery than the wild-type streptavidin-agarose matrix. This difference can possibly be attributed to the difference in accessibility of the immobilized streptavidin in the matrices. The SBPM18-affigel and wild-type streptavidin matrices have 15- and 7-atom spacers, respectively. The longer spacer of SBPM18-affigel may allow the immobilized streptavidin to have more dimeric sites accessible to interact with the SBP tag and hence better binding capacity. This feature can be more obvious under the overloading condition. To take advantage of the full binding strength between the SBP-tagged proteins and the matrices, the amounts of SBP-tagged protein loaded should not exceed the capacity of the column. As shown in this study, it is appropriate to load the amount of the SBP-tagged proteins that is equivalent to 20% of the theoretical column capacity to avoid overloading the column.

Advantage of SBPM18 Over the Wild-Type Streptavidin in Purifying SBP-Tagged and Biotinylated Proteins.

Inability to reuse the wild-type streptavidin matrix to purify SBP tagged or biotinylated proteins is the major limitation. Furthermore, presence of biotin in the protein samples is another common complication. This often leads to lower column binding capacity and poor recovery because of the irreversible poisoning of some of the streptavidin molecules in the matrix if biotin is not removed by dialysis. This mistake is particularly common for the new or inexperienced users. However, when the problem is recognized, the damage to the matrix has been done. SBPM18 overcomes this problem and allows many rounds of reuse of the matrix.

Advantage of the SBP Tag Over Other Tags.

Affinity tag in recombinant proteins is commonly used for affinity purification—indeed, many tags are available. Among these, His-tag is one of the most popular tags used. Depending on the matrices used, the binding affinity of the His-tag protein in general is relatively low (K$_d$~µM) (Nieba et al., 1997). Furthermore, many metal binding proteins and proteins with naturally surface exposed histidine residues can bind non-specifically to the matrix. Purity of the purified His-tag proteins is usually in the range of 80%. In some reported cases, addition of His-tag can interfere with protein folding (Halliwell et al., 2001; Pekrun et al., 1995; Ledent et al., 1997), affect substrate binding (Slessor et al., 2010; Freydank et al., 2008) and cause heterogeneity of the tagged proteins and their biological activities (Narmandakh and Bearne, 2010). To improve purity, a double-His tag (two His tags separated by a spacer) approach has been developed (Khan et al., 2006). However, in this study, the double His-tagged green fluorescent protein has been reported to be resolved into two different peaks during elution.

Besides the SBP tag, two streptavidin binding tags are available. The first one is a 15-amino-acid nano-tag (K$_d$~4 nM) (Lamla and Erdmann, 2004). Because of its mode of interaction with streptavidin, this tag has to be localized at the N-terminus of the recombinant protein (Perbandt et al., 2007). Furthermore, a formylated methionine is required at the N-terminus for high-affinity interactions. Consequently, the recombinant proteins can only be produced from prokaryotes. The second one is strep-tag II. It requires the use of an engineered streptavidin designated Strep-Tactin to bring the binding affinity to μM range (Voss and Skerra, 1997). Similar to the principle of the SBP tag, a new tag known as strep-tag III (or One-STrEP-tag) has been developed (Juntila et al., 2005). This tag has two strep-tag II sequences separated by a linker and can bind to Strep-Tacin with a much higher affinity. Although strep-tag containing proteins can be eluted off from the matrix by using desthiobiotin, the binding capacity of the column tends to decrease with use. This is probably because of the presence of contaminating biotin in the desthiobiotin supply. Furthermore, to achieve better recovery of the strep-tag proteins, the use of biotin in elution is recommended. Since Strep-Tacin binds tightly to biotin in a similar manner as the wild-type streptavidin, regeneration of the column would not be feasible.

Other Possible Applications.

Development of SBPM18 revolutionizes the technology in purification of SBP tagged or biotinylated protein to high purity and recovery in one step and allows reuse of the matrix for many rounds. SBPM18 can also be immobilized to different platforms such as protein arrays, ELISA plates, magnetic beads, biosensor chips and bioreactors for different applications. Furthermore, horseradish peroxidase, alkaline phosphatase or fluorescent dye conjugated SBPM18 can potentially be applied for probing SBP-tagged or biotinylated proteins in Western blots or for cell imaging. Reprobing of these proteins by antibodies can be done easily since SBPM18 can be gently stripped off.

Example 4

Comparative Example

Advantage of SBPM18 Over Streptavidin Mutein from Roche.

A streptavidin mutein from Roche is reusable for affinity purification of biotinylated biomolecules (U.S. Pat. No. 6,312,916 B1). This mutein has three mutations including S27R, S45R and L110W. Interaction between SBP and streptavidin analyzed by the Molegro program suggests that all three residues in streptavidin are involved in binding the SBP tag. The strength of interactions is in the following order: L110>>S45>>S27. Furthermore, unlike SBPM18, Ser-27 in the Roche mutein is changed to arginine instead of alanine. Since the arginine side chain is much bulkier, the negative impact of this mutation on SBP tag binding can be more dramatic.

The inventors sought to determine whether the Roche streptavidin mutein matrix (Cat. #03708152001) could bind β-lactamase-SBP. The column size was 0.6 ml, pre-equilibrated with the loading buffer containing 0.4 M ammonium sulfate. The results showed that β-lactamase-SBP could not be retained in the column and appeared in the flow-through and wash fractions. Leakage of streptavidin subunits from the matrix was observed. Thus, it was concluded that the Roche matrix cannot bind β-lactamase-SBP.

Next, the inventor sought to determine whether the Roche mutein matrix could bind pure biotinylated maltose binding protein. The column size was 0.3 ml, pre-equilibrated with the loading buffer containing 0.4 M ammonium sulfate. Pure biotinylated maltose binding protein in buffer containing 0.4 M ammonium sulfate was loaded to the Roche matrix equilibrated with the loading buffer containing 0.4 M ammonium sulfate. Biotinylated protein could be observed in both the wash fractions and the elution fractions. The washing buffer also contained 0.4 M ammonium sulfate. Thus, biotinylated maltose binding protein cannot be retained in the Roche streptavidin matrix very well.

Next, the inventor assessed leakage of streptavidin subunits from the Roche matrix-Purification of biotinylated BSA (1.7 biotin/protein). SAV subunits can be observed in the flow through, wash and elution fractions. Thus, leakage appear to be an issue.

It is not a surprise that the Roche streptavidin mutein matrix failed to bind β-lactamase-SBP. For purification of biotinylated proteins, biotinylated maltose binding protein was used as a model for the study. This protein has a biotinylation tag and therefore has only one biotin per protein. Unlike multi-biotinylated proteins, there will be no avidity effect in the binding. Purification of this protein requires sufficient interaction strength between the engineered streptavidin and biotinylated protein. SBPM18-affigel can purify this protein with great ease and high recovery. No special buffers are needed. In contrast, leakage of this protein in both the flow-through and wash fractions was observed with the Roche streptavidin mutein matrix. Even with addition of ammonium sulfate to the loading and washing buffers as recommended by the manufacture to strengthen the binding of the biotinylated protein to the matrix, leakage of the biotinylated maltose binding protein could still be observed. Furthermore, streptavidin subunits could also be detected in flow-through or even in elution fractions depending on the amounts of matrix used (data not shown).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 5,928,906
U.S. Pat. No. 6,312,916 B1
Ausubel et al., *Current Protocols in Molecular Biology*, Greene Publishing Associates and Wiley Interscience, N.Y., 1994.
Burckstummer et al., *Nat. Methods*, 3:1013-1019, 2006.
Capaldi et al., *Biochem. Biophys. Res. Comm.*, 74(2):425-433, 1977.
Chilkoti et al., *Proc. Natl. Acad. Sci. USA*, 92:1754-1758, 1995.
Freitag et al., *Protein Sci.*, 6(6):1157-1166, 1997.
Freydank et al., *Proteins*, 72:173-183, 2008.
Frohman et al., *Proc. Natl. Acad. Sci. USA*, 85:8998-9002, 1988.

Green, *Methods Enzymol.,* 184:51-67, 1990.
Guex and Peitsch, *Electrophoresis,* 18:2714-2723, 1997.
Halliwell et al., *Anal. Biochem.,* 295:257-261, 2001.
Harding and Jumel, *Curr. Protoc. Protein Sci.* 7:Unit 7.8, 2001.
Johnson et al., In: *Biotechnology And Pharmacy,* Pezzuto et al. (Eds.), Chapman and Hall, NY, 1993.
Junttila et al., *Proteomics,* 5:1199-1203, 2005.
Keefe et al., *Protein Expr. Purif.,* 23:440-446, 2001.
Khan et al., *Anal. Chem.,* 78:3072-3079, 2006.
Kim et al., *BMC Biochem.,* 11:50, 2010.
Klumb et al., *Biochemistry,* 37:7657-7663, 1998.
Kobayashi et al., *PLoS ONE,* 3:e3822, 2008.
Krieger et al., *Proteins,* 47:393-402, 2002.
Kyte and Doolittle, *J. Mol. Biol.,* 157(1):105-132, 1982.
Lamla and Erdmann, *Protein Expr. Purif.,* 33:39-47, 2004.
Ledent et al., *FEBS Lett.,* 413:194-196, 1997.
Li et al., *Protein Sci.,* 20:140-149, 2011.
Narmandakh and Bearne, *Protein Expr. Purif.,* 69:39-46, 2010.
Nieba et al., *Anal. Biochem.,* 252:217-228, 1997.
Pekrun et al., *Eur. J. Biochem.,* 234:811-818, 1995.
Perbandt et al., *Proteins,* 67:1147-1153, 2007.
Qureshi and Wong, *Protein Expr. Purif.,* 25:409-415, 2002.
Qureshi et al., *J. Biol. Chem.,* 276(49):46422-46428, 2001.
Sambrook, et al., Molecular Cloning: A Laboratory Manual, 2$^{nd}$ Ed., Cold Spring Harbor, N.Y., 1989.
Seki et al., *J. Biosci. Bioeng.,* 108:30-35, 2009.
Slessor et al., *Citrobacter braakii. Bioorg. Chem.,* 38:81-86, 2010.
Thomsen and Christensen, *J. Med. Chem.,* 49(11): 3315-3321, 2006.
Van Leene et al., *Trends Plant Sci.,* 13:517-520, 2008.
Voss and Skerra, *Protein Eng.,* 10:975-982, 1997.
Wilchek and Bayer, *Methods Enzymol.,* 184: 5-13, 1990.
Wilson et al., *Proc. Natl. Acad. Sci. USA,* 98:3750-3755, 2001.
Wu and Wong, *Appl. Environ. Microbiol.,* 68:1102-1108, 2002.
Wu and Wong, *J. Biol. Chem.,* 280(24): 23225-23231, 2005a.
Wu and Wong, *J. Biol. Chem.,* 280:23225-23231, 2005b.
Wu et al., *Appl. Environ. Microbiol.,* 68(7):3261-3269, 2002.
Xiao et al., *ACS Nano,* 3:2163-2170, 2009.

The invention claimed is:

1. A streptavidin mutein comprising a substitution of the glycine at residue 48 corresponding to full-length wild-type streptavidin (SEQ ID NO:1), wherein said substitution comprises threonine, aspartic acid, glutamic acid, asparagine or glutamine.

2. The mutein of claim 1, further comprising a serine to alanine substitution at residue 27.

3. The mutein of claim 1, wherein said mutein lacks a signal sequence.

4. The mutein of claim 3, wherein said mutein consists of 159 streptavidin residues.

5. The mutein of claim 4, wherein said mutein has the sequence of SEQ ID NO:3.

6. The mutein of claim 1, wherein said mutein comprises a signal sequence.

7. The mutein of claim 6, wherein said mutein consists of 188 streptavidin residues.

8. The mutein of claim 7, wherein said mutein has the sequence of SEQ ID NO:5.

9. The mutein of claim 1, further comprising a non-streptavidin sequence fused to said mutein.

10. The mutein of claim 9, wherein said non-streptavidin sequence is a cellulose binding domain, a chitin binding domain, a dextran binding domain, a silica binding peptide, a gold binding peptide or ferritin.

11. A nucleic acid encoding a streptavidin mutein comprising a substitution of the glycine at residue 48 corresponding to full-length wild-type streptavidin (SEQ ID NO:1), wherein said substitution comprises threonine, aspartic acid, glutamic acid, asparagines or glutamine.

12. The nucleic acid of claim 11, further comprising a serine to alanine substitution at residue 27.

13. The nucleic acid of claim 11, wherein said mutein lacks a signal sequence.

14. The nucleic acid of claim 13, wherein said mutein consists of 159 streptavidin residues.

15. The nucleic acid of claim 11, wherein said mutein comprises a signal sequence.

16. The nucleic acid of claim 11, further encoding a non-streptavidin sequence fused to said mutein.

17. A method of binding a biotin molecule comprising contacting a biotin molecule with a streptavidin mutein comprising a substitution of the glycine at residue 48 corresponding to full-length wild-type streptavidin (SEQ ID NO:1), wherein said substitution comprises threonine, aspartic acid, glutamic acid, asparagine or glutamine.

18. A method of binding a streptavidin binding peptide (SBP) comprising contacting a SBP molecule with a streptavidin mutein comprising a substitution of the glycine at residue 48 corresponding to full-length wild-type streptavidin (SEQ ID NO:1), wherein said substitution comprises threonine, aspartic acid, glutamic acid, asparagine or glutamine.

19. A method of purifying a biotin- or SBP-tagged protein from a mixture comprising:
 (a) providing a protein mixture comprising a biotin- or SBP-tagged protein;
 (b) contacting said protein mixture with a streptavidin mutein comprising a substitution of the glycine at residue 48 corresponding to full-length wild-type streptavidin (SEQ ID NO:1), wherein said substitution comprises threonine, aspartic acid, glutamic acid, asparagine or glutamine; and
 (c) separating said biotin- or SBP-tagged protein bound to said streptavidin mutein.

20. A method of binding a biotin- or SBP-tagged protein to a solid matrix or support comprising:
 (a) providing a biotin- or SBP-tagged protein; and
 (b) contacting said protein with a solid matrix or support onto which a streptavidin mutein comprising a substitution of the glycine at residue 48 corresponding to full-length wild-type streptavidin (SEQ ID NO:1), wherein said substitution comprises threonine, aspartic acid, glutamic acid, asparagine or glutamine, is disposed.

* * * * *

SEQUENCE LISTING

```
<160> NUMBER OF SEQ ID NOS: 15

<210> SEQ ID NO 1
<211> LENGTH: 159
<212> TYPE: PRT
<213> ORGANISM: Streptomyces avidinii

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 480
<212> TYPE: DNA
<213> ORGANISM: Streptomyces avidinii

<400> SEQUENCE: 2
gacccgagca aagattctaa agcacaagta tctgctgcag aagcgggcat tacgggcacg      60
tggtataatc agctgggcgc tacgtttatt gttacggccg gcgcagatgg agctctgacg     120
```

```
ggcacgtatg aaagcgcggt tacaaatgca gaatctagat acgttcttac aggaagatat    180
gattctgcac ctgcaacaga tggatccggc acggcactgg gctggacagt tgcatggaaa    240
aacaattatc gcaacgcaca tagcgccacg acgtggtctg gccaatatgt tggcggtgca    300
gaagcacgca ttaacacaca gtggcttctg acgtccggaa caacagaagc aaatgcatgg    360
aaaagtactc ttgttggaca tgatacattt acaaagtta  aacctagcgc agcatctatc    420
gatgcagcga aaaagcagg  agttaacaat ggcaatcctt tagatgcagt tcaacaataa    480
```

```
<210> SEQ ID NO 3
<211> LENGTH: 159
<212> TYPE: PRT
<213> ORGANISM: Artificial sequence
<220> FEATURE:
<223> OTHER INFORMATION: Synthetic streptavidin mutein

<400> SEQUENCE: 3

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ala Thr Phe Ile Val Thr
            20                  25                  30

Ala Gly Ala Asp Gly Ala Leu Thr Gly Thr Tyr Glu Ser Ala Val Thr
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

```
<210> SEQ ID NO 4
<211> LENGTH: 567
<212> TYPE: DNA
<213> ORGANISM: Artificial sequence
<220> FEATURE:
<223> OTHER INFORMATION: Synthetic streptavidin mutein

<400> SEQUENCE: 4
atgaatatca aaaaattcgc taagcaagct acagtcctta catttacaac agcgctgctt    60
gccgggggcg ccacccaggc ctttgctgac ccgagcaaag attctaaagc acaagtatct    120
gctgcagaag cgggcattac gggcacgtgg tataatcagc tgggcgctac gtttattgtt    180
acggccggcg cagatggagc tctgacgggc acgtatgaaa gcgcggttac aaatgcagaa    240
tctagatacg ttcttacagg aagatatgat tctgcacctg caacagatgg atccggcacg    300
gcactgggct ggacagttgc atggaaaaac aattatcgca acgcacatag cgccacgacg    360
tggtctggcc aatatgttgg cggtgcagaa gcacgcatta acacacagtg gcttctgacg    420
tccggaacaa cagaagcaaa tgcatggaaa agtactcttg ttggacatga tacatttaca    480
```

```
aaagttaaac ctagcgcagc atctatcgat gcagcgaaaa aagcaggagt taacaatggc    540
aatcctttag atgcagttca acaataa                                        567
```

<210> SEQ ID NO 5
<211> LENGTH: 188
<212> TYPE: PRT
<213> ORGANISM: Artificial sequence
<220> FEATURE:
<223> OTHER INFORMATION: Synthetic streptavidin mutein

<400> SEQUENCE: 5

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Asp Pro Ser
            20                  25                  30

Lys Asp Ser Lys Ala Gln Val Ser Ala Glu Ala Gly Ile Thr Gly
        35                  40                  45

Thr Trp Tyr Asn Gln Leu Gly Ala Thr Phe Ile Val Thr Ala Gly Ala
    50                  55                  60

Asp Gly Ala Leu Thr Gly Thr Tyr Glu Ser Ala Val Thr Asn Ala Glu
65                  70                  75                  80

Ser Arg Tyr Val Leu Thr Gly Arg Tyr Asp Ser Ala Pro Ala Thr Asp
                85                  90                  95

Gly Ser Gly Thr Ala Leu Gly Trp Thr Val Ala Trp Lys Asn Asn Tyr
            100                 105                 110

Arg Asn Ala His Ser Ala Thr Thr Trp Ser Gly Gln Tyr Val Gly Gly
        115                 120                 125

Ala Glu Ala Arg Ile Asn Thr Gln Trp Leu Leu Thr Ser Gly Thr Thr
    130                 135                 140

Glu Ala Asn Ala Trp Lys Ser Thr Leu Val Gly His Asp Thr Phe Thr
145                 150                 155                 160

Lys Val Lys Pro Ser Ala Ala Ser Ile Asp Ala Ala Lys Lys Ala Gly
                165                 170                 175

Val Asn Asn Gly Asn Pro Leu Asp Ala Val Gln Gln
            180                 185
```

<210> SEQ ID NO 6
<211> LENGTH: 130
<212> TYPE: PRT
<213> ORGANISM: Artificial sequence
<220> FEATURE:
<223> OTHER INFORMATION: Synthetic streptavidin mutein

<400> SEQUENCE: 6

```
Ala Ala Glu Ala Gly Ile Thr Gly Thr Trp Tyr Asn Gln Leu Gly Ala
1               5                   10                  15

Thr Phe Ile Val Thr Ala Gly Ala Asp Gly Ala Leu Thr Gly Thr Tyr
            20                  25                  30

Glu Ser Ala Val Thr Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
```

```
              100                 105                 110
Leu Val Gly His Asp Thr Phe Thr Lys Val Lys Pro Ser Ala Ala Ser
        115                 120                 125

Ile Asp
    130

<210> SEQ ID NO 7
<211> LENGTH: 390
<212> TYPE: DNA
<213> ORGANISM: Artificial sequence
<220> FEATURE:
<223> OTHER INFORMATION: Synthetic streptavidin mutein

<400> SEQUENCE: 7
gctgcagaag cgggcattac gggcacgtgg tataatcagc tgggcgctac gtttattgtt      60
acggccggcg cagatggagc tctgacgggc acgtatgaaa gcgcggttac aaatgcagaa     120
tctagatacg ttcttacagg aagatatgat tctgcacctg caacagatgg atccggcacg     180
gcactgggct ggacagttgc atggaaaaac aattatcgca acgcacatag cgccacgacg     240
tggtctggcc aatatgttgg cggtgcagaa gcacgcatta acacacagtg gcttctgacg     300
tccggaacaa cagaagcaaa tgcatggaaa agtactcttg ttggacatga tacatttaca     360
aaagttaaac ctagcgcagc atctatcgat                                      390

<210> SEQ ID NO 8
<211> LENGTH: 126
<212> TYPE: PRT
<213> ORGANISM: Artificial sequence
<220> FEATURE:
<223> OTHER INFORMATION: Synthetic streptavidin mutein

<400> SEQUENCE: 8

Glu Ala Gly Ile Thr Gly Thr Trp Tyr Asn Gln Leu Gly Ala Thr Phe
1               5                   10                  15

Ile Val Thr Ala Gly Ala Asp Gly Ala Leu Thr Gly Thr Tyr Glu Ser
            20                  25                  30

Ala Val Thr Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 9
<211> LENGTH: 378
<212> TYPE: DNA
<213> ORGANISM: Artificial sequence
<220> FEATURE:
<223> OTHER INFORMATION: Synthetic streptavidin mutein

<400> SEQUENCE: 9
gaagcgggca ttacgggcac gtggtataat cagctgggcg ctacgtttat tgttacggcc      60
ggcgcagatg gagctctgac gggcacgtat gaaagcgcgg ttacaaatgc agaatctaga    120
```

```
tacgttctta caggaagata tgattctgca cctgcaacag atggatccgg cacggcactg    180
ggctggacag ttgcatggaa aaacaattat cgcaacgcac atagcgccac gacgtggtct    240
ggccaatatg ttggcggtgc agaagcacgc attaacacac agtggcttct gacgtccgga    300
acaacagaag caaatgcatg gaaaagtact cttgttggac atgatacatt tacaaaagtt    360
aaacctagcg cagcatct                                                  378
```

```
<210> SEQ ID NO 10
<211> LENGTH: 59
<212> TYPE: PRT
<213> ORGANISM: Artificial Sequence
<220> FEATURE:
<223> OTHER INFORMATION: Synthetic peptide

<400> SEQUENCE: 10

Cys Gly Gly Gly Gly Ser Thr Ser Gly Gly Ser Thr Ser Gly Gly Ser
1               5                   10                  15

Thr Ser Gly Gly Gly Met Asp Glu Lys Thr Thr Gly Trp Arg Gly Gly
            20                  25                  30

His Val Val Glu Gly Leu Ala Gly Glu Leu Glu Gln Leu Arg Ala Arg
        35                  40                  45

Leu Glu His His Pro Gln Gly Gln Arg Glu Pro
    50                  55

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Gly His Val Val Glu Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Leu Glu His His Pro Gln Gly Gln
1               5

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Leu Ala Gly Glu Leu Glu Gln Leu Arg Ala Arg
1               5                   10

<210> SEQ ID NO 14
<211> LENGTH: 38
<212> TYPE: PRT
<213> ORGANISM: Artificial Sequence
<220> FEATURE:
<223> OTHER INFORMATION: Synthetic Peptide
```

-continued

```
<400> SEQUENCE: 14

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 15
<211> LENGTH: 25
<212> TYPE: PRT
<213> ORGANISM: Artificial Sequence
<220> FEATURE:
<223> OTHER INFORMATION: Synthetic peptide

<400> SEQUENCE: 15

Gly His Val Val Glu Gly Leu Ala Gly Glu Leu Glu Gln Leu Arg Ala
1               5                   10                  15

Arg Leu Glu His His Pro Gln Gly Gln
            20                  25
```